United States Patent [19]

Sinn et al.

[11] Patent Number: 5,308,604
[45] Date of Patent: May 3, 1994

[54] CONJUGATES FOR TUMOR LOCALIZATION AND/OR TUMOR THERAPY

[75] Inventors: Hansjörg Sinn, Wiesloch; Hans-Hermann Schrenk, Zeiskam; Wolfgang Maier-Borst, Dossenheim; Eckhard Friedrich, Ilbesheim; Georgi Graschew, Heidelberg; Dieter Wörhle, Bremen, all of Fed. Rep. of Germany

[73] Assignee: Deutsches Krebsforschungsinstitut, Heidelberg, Fed. Rep. of Germany

[21] Appl. No.: 859,273

[22] Filed: Mar. 26, 1992

Related U.S. Application Data

[63] Continuation of Ser. No. 734,123, Jul. 25, 1991, abandoned, which is a continuation of Ser. No. 509,810, Apr. 17, 1990, abandoned.

[30] Foreign Application Priority Data

Apr. 19, 1989 [DE] Fed. Rep. of Germany ....... 3912792

[51] Int. Cl.$^5$ .................... A61K 49/02; A61K 43/00; A61K 49/00
[52] U.S. Cl. ..................... 424/1.53; 424/7.1; 424/9; 424/1.69; 530/363; 530/409; 530/411
[58] Field of Search .................. 424/1.1, 7.1, 9, 85.91; 530/363, 409, 411

[56] References Cited

U.S. PATENT DOCUMENTS

| | | | |
|---|---|---|---|
| 4,081,244 | 3/1978 | Polito et al. ............... | 424/1.1 X |
| 4,228,240 | 10/1980 | Dawson et al. ............. | 435/188 |
| 4,466,951 | 8/1984 | Pittman ..................... | 424/1.1 |
| 4,735,210 | 4/1988 | Goldenberg ................ | 128/654 |
| 4,859,449 | 8/1989 | Mattes ...................... | 424/9 |
| 5,087,696 | 2/1992 | Parker et al. ............... | 540/465 |
| 5,162,507 | 11/1992 | Wolfe et al. ................ | 530/412 |

OTHER PUBLICATIONS

S. A. Ali, et al., "Synthesis and Radioiodination of Tyramine Cellobiose for Labeling Monoclonal Antibodies," Nucl. Med. Biol., 15(5):557–561 (1988).
R. C. Pittman, et al., "A Radioiodinated, Intracellularly Trapped Ligand for Determining the Sites of Plasma Protein Degradation In Vivo," Biochem J., 212:791–800 (1983).

*Primary Examiner*—Robert L. Stoll
*Assistant Examiner*—John M. Covert
*Attorney, Agent, or Firm*—Finnegan, Henderson, Farabow, Garrett & Dunner

[57] ABSTRACT

The invention relates to conjugates composed of
a) at least one polyalcohol or a derivatized polyalcohol,
b) at least one active agent,
c) at least one linker and
d) a protein, wherein the polyalcohol(s) or the derivatized polyalcohol(s) are polyalcohols or derivatized polyalcohols which are not recognized by the defense system of an organism as exogenous, and the protein is a protein which can be taken up by the tumor specifically or non-specifically, and is not recognized by the defense system of an organism as exogenous. These conjugates are suitable for, on the one hand, making possible a very sensitive method in nuclear medicine for the diagnosis of tumors and, on the other hand, for example also offering new methods for diagnosing tumors in X-ray diagnosis, computerized tomography, nuclear spin tomography, electron spin resonance spectroscopy or electron microscopy.

9 Claims, 1 Drawing Sheet

CONJUGATES FOR TUMOR LOCALIZATION AND/OR TUMOR THERAPY

This application is a continuation of application Ser. No. 07/734,123, filed Jul. 25, 1991, now abandoned which is a continuation of application Ser. No. 07/509,810, filed Apr. 17, 1990, now abandoned.

DESCRIPTION

Conjugates for tumor localization and/or tumor therapy, a process for the preparation thereof, and diagnostic and/or therapeutic agents containing these.

The invention relates to conjugates which, by reason of their composition, have an increased biological half-life and preferentially accumulate in tumor tissue. These conjugates are suitable for, on the one hand, making possible a very sensitive method in nuclear medicine for the diagnosis of tumors and, on the other hand, for example also offering new methods for diagnosing tumors in X-ray diagnosis, computerized tomography, nuclear spin tomography, electron spin resonance spectroscopy or electron microscopy. The integration of photoactive components into the conjugates according to the invention makes these additionally suitable for laser fluorescence diagnosis and for photodynamic therapy of malignant tumors. It is furthermore possible to utilize the great accumulation of the conjugates according to the invention in tumors for transporting cytostatics to the tumor.

A technique for localizing tumors which is widely used nowadays makes use of the specificity of particular antibodies against tumor-associated antigens. Antibodies of this type, and monoclonal antibodies are particularly used for this purpose, can be directly labeled relatively easily with the radioactive nuclides of iodine. Labeling with other radioactive nuclides suitable for diagnosis or therapy, such as indium-111, proves to be somewhat more difficult because these can usually be linked to the antibodies only via suitable chelating agents (for example DTPA). This chelating technique is nowadays applied more or less successfully.

However, the antibodies labeled in this way have the great disadvantage that, after injection has taken place, the radioactive nuclides or the chelated radioactive nuclides are cleaved off the relevant antibody in the body and thus do not finish up in the target organ at all. In particular, the chelated metals (such as indium111-DTPA) are trapped in the liver and accumulate there. It is obvious to suppose that the indium-111-DPTA complex which is cleaved off remains in the defense system (reticuloendothelial system). This is why it is impossible to detect accumulations in tumors in the region of the liver or in the bone marrow. It would be desirable if it were possible to increase even further the specific accumulation at the tumor. A method for avoiding storage of the radionuclides linked via chelating agents in the reticuloendothelial system would be a very considerable technical advance. These two steps in development would considerably increase the efficiency and, in particular, also the diagnostic reliability of tumor detection. However, they would be even more important for the use of radioactively labeled substances in therapy. All the individual treatments which have been carried out to date had the disadvantage that, out of consideration for the organs to be protected, it was necessary to choose a relatively low tumor dose. Only with a maximally selective accumulation of the transported radionuclide and a long residence time in the tumor does it appear possible for there to be a high radiation dobe at the tumor with substantial protection of the healthy tissue.

Pittman et al. (Biochem. J. (1983), 212, 791–800) describe lipoprotein catabolism investigations in which the lipoproteins are labeled with a tyramine-cellobiose label.

Ali et al. (Nucl. Ned. Biol., Vol. 15, No. 5, pp. 557–561, (1988)) and Walch et al. (Proc. 7th Intern. Symp. on Radiopharm. Chem., 1988, Paper 120) reported use of a tyramine-cellobiose antibody conjugate which was labeled in the tyramine portion with radioactive iodine. Although it was found with this that the percentage activity in the tumor increased, the liver storage still remained too high.

Maxwell et al. (J. Biol. Chem., Vol. 263, No. 28, pp. 14122 to 14127, (1988)) describe an inulin-$^{125}$I-tyramine label for long-lived circulating proteins. It is then possible, by coupling this label to circulating proteins such as rat serum albumin (RSA), to localize those sites in the organism where the circulating proteins are broken down (catabolism of plasma proteins). Maxwell et al. found that relatively large glycoconjugates, such as the inulin conjugate described, are better suited for catabolism investigations than smaller glycoconjugates because these large conjugates precipitate at the site of breakdown of the plasma protein and are transported away to only a small extent or not at all.

It has now been found, surprisingly, that conjugates composed of
a) at least one polyalcohol or a derivatized polyalcohol,
b) at least one active agent,
c) at least one linker and
d) a protein,
wherein the polyalcohol(s) or the derivatized polyalcohol(s) are polyalcohols or derivatized polyalcohols which are not recognized by the defense system of an organism as exogenous, and the protein is a protein which can be taken up by the tumor specifically or non-specifically, and is not recognized by the defense system of an organism as exogenous, are excellently suited for tumor diagnosis and/or tumor therapy.

The invention furthermore relates to a process for the preparation of the conjugates according to the invention, and to tumor diagnostic and tumor therapeutic agents, methods for the diagnosis of tumors and methods for the treatment of tumors using the conjugates according to the invention.

Figure 1:
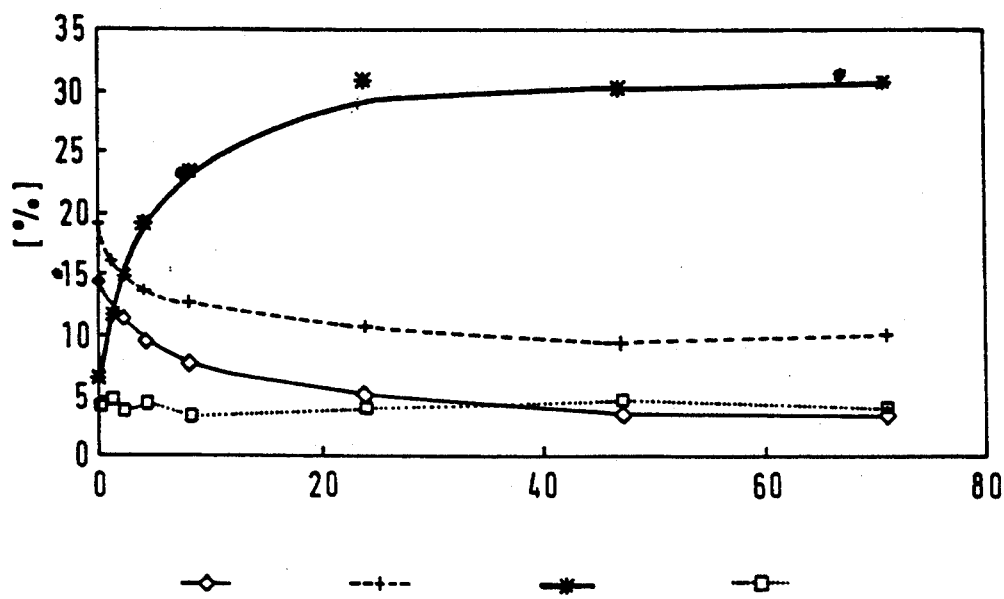
FIG. 1. The percentage radioactivity distribution (based on administered radioactivity) in the heart (— ◊ —), liver (—+—), tumor (—*—) and muscle (—□—) of $^{131}$I-TDS-RSA (tryamine-deoxysorbitol coupled to rat serum albumin) measured as a function of time in BD IX rats with implanted ovraian carcinoma. For experimental details, see "Pharmacological Examples."

A conjugate means a substance which is held together by chemical bonds and is composed of several different molecules with characteristic properties. In this connection, the chemical bonds can be ionic, covalent or coordinate, preferably covalent.

The conjugates according to the invention have the advantage that they are not regarded by the defense system of the organism as exogenous and, accordingly, are trapped, broken down and excreted by organs such as the liver, or are deposited there, to only a small extent or not at all. This is achieved by the protective function of the polyalcohol(s) which screens the usually exogenous active component—that is to say the active agent(s)—so that they are not recognized by the defense system of the body. In order now to ensure that the active component which has been masked in this way is selectively transported to tumor tissues and, moreover, remains there, a protein which is taken up by the tumor specifically or non-specifically is linked to this masked active component via a linker—also called a spacer. The protein itself is now chosen such that, on the one hand, it is not recognized by the defense system of the body and, on the other hand, it accumulates specifically or non-specifically in tumors. If a conjugate with a composition of this type is now injected, it remains in the circulation unrecognized by the defense system of the body until it is taken up specifically or non-specifically to a high percentage by tumor cells. In the tumor cells the protein is then either catabolized or it binds specifically to the tumor-associated antigens. If it is broken down, in the final analysis the conjugate which has been reduced by the protein remains in the tumor cell, because it continues to be unrecognized as exogenous because of its masking polyalcohol protective groups and, accordingly, is not ejected from the tumor cells either. In both cases—conjugate with protein which can be broken down and conjugate with antigen-specific protein—the conjugate accumulates in the tumor (cumulative label) and can be located via its active agent or its active agents by use of suitable methods or can display its therapeutic action directly at the site of the tumor, depending on the nature of the active agent. These conjugates according to the invention display a surprisingly high tumor accumulation rate, which is about 25–30 %, or more, of the administered dose in experimental animals, with, at the same time, an extremely low accumulation rate in the reticuloendothelial system.

A non-immunologically recognizable polyalcohol means those polyalcohols or polyalcohol derivatives which are not recognized by the endogenous defense system as exogenous and, as a consequence, are trapped by the appropriate organs to only an inconsiderable extent or not at all.

Polyalcohols which are preferably employed are those of the formula I

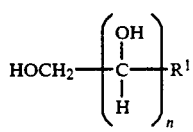

in which
$R^1$ is $CH_2OH$, CHO or $CH_2NH_2$, and
n is greater than or equal to 1, preferably n is 1–10, particularly preferably 3–6,
and in which a

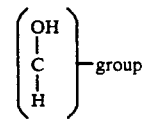

can be replaced by CO and in which zero, one or more OH groups can be replaced by $NH_2$, $^{19}F$, $C^{19}F_3$, mono- or poly-$^{19}F$-substituted $C_1$–$C_4$-alkyl or mono-, di-, tri-, tetra- or penta-$^{19}F$-substituted phenyl.

Equally suitable are glucose, fructose, maltose or sucrose, with at least one OH group in these compounds being replaced by $^{19}F$, $C^{19}F_3$, mono- or poly-$^{19}F$-substituted $C_1$–$C_4$-alkyl or mono-, di-, tri-, tetra- or penta-$^{19}F$-substituted phenyl.

Examples of such polyalcohols are glucose, fructose, disaccharides such as sucrose, maltose, and sorbitol and glyceraldehyde. Where liver storage is unimportant or of only minor importance for the diagnosis of particular tumors, polyalcohols such as galactose are also suitable.

An active agent means a compound which either is able to emit a signal to an external scanning device or is able to have a direct or indirect therapeutic effect on tumor tissue, or else is able to exert both functions simultaneously. It is just as good for the active agent to be bi- or multifunctional, i.e. it can emit two or more different signals which are then picked up by different scanning devices.

Compounds able to emit a signal to an external scanning device are preferably those of the formula II

in which
$R^2$ is $NH_2$, $C_1$–$C_4$-alkylamino or CHO, and
$R^3$ is $NO_2$, I $NH_2$, OH or NCS, and
$R^4$ is $^{131}I$, $^{123}I$, $^{19}F$, $C^{19}F_3$, OH or H, and
n is 1 to 4.

For example, it is possible to employ radioactively labeled substances such as $^{123}I$- or $^{131}I$-labeled tyramine or cyclams (cyclic amines) which are able to complex metals such as In, Ga, Gd, Sm, Y, Re, Rh, Ru or Pt.

If compounds of this type are incorporated in the conjugate according to the invention, then these conjugates are suitable for scintigraphic visualization with γ camera or SPECT (single photon emission computerized tomography) systems. Other compounds which are able to emit a signal to an external scanning device are, for example, fluorescence labels or active agents which are suitable for use in computerized tomography (CT). Examples suitable for this are highly iodinated fluorescein isothiocyanates (FITC). Or active agents which are suitable for use in nuclear spin computerized tomography (NMR). Examples of this are fluorinated aliphatic (—$CF_3$) or aromatic ($\phi$-(F)$_4$) groups ($\phi$-phenyl). Or active agents which are suitable for use in electron spin resonance spectroscopy (ESR). Examples of this are heterocyclic ring systems with radical characteristics such as 4(-4-amino-2,2,6,6-tetramethyl-1-piperidinyloxy. Or active agents which are suitable for use in neutron capture therapy (NCT). Examples of this are boron-containing compounds such as $Na_2{}^{10}B_{12}H_{11}\text{-}SH$ or other boron-containing derivatives of porphyrins, phthalocyanins, naphthalocyanins etc.

External scanning devices are devices of the state of the art which convert signals emitted by active agents into information which can be evaluated. Examples of this are γ camera or SPECT systems which capture the γ rays or photons emitted by the radioactively labeled compounds and convert them into images (scintigrams).

Computerized tomographs are instruments which record the different attenuation of an X-ray penetrating through the organism and convert it into image information. The different attenuation of the X-ray derives from the different distribution of contrast media in the tissue. Electron and nuclear spin tomographs are instruments which detect the changes in spin of electrons and atomic nuclei, respectively, in strong, aligned magnetic fields and convert them into image information.

A linker means, within the meaning of the invention, those compounds which can be employed as coupling member or spacer between protein and active agent. These are usually bifunctional compounds which use one functional group to enter into a chemical bond with the active agent and use the second functional group to enter into a chemical bond with the protein which is taken up specifically or non-specifically by the tumor. Where it can be contrived (for example by radioiodine labeling), the linker can also assume the function of the active agent. Examples of linkers are:

2,4-dichloropyrimidine:

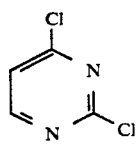

4,4'-diisothiocyanoato-2,2'-stilbenedisulfonic acid (DIDS):

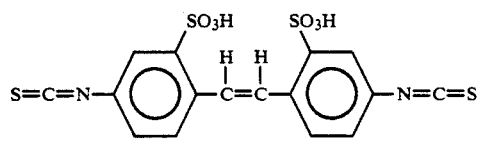

cyanuric chloride (2,4,6-trichloro-s-triazine):

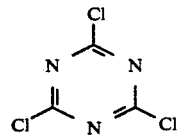

A protein which is taken up specifically or non-specifically by the tumor is an endogenous (autologous) protein which is not trapped by the defense system of the body and is subject only to natural catabolism and meets the following conditions:
a) it should have a maximally long biological half-life, preferably of 2 to 30 days, in particular of 5 to 10 days;
b) it should be above the glomerular exclusion limit, preferably have a molecular weight above 50 kD, particularly preferably above 60 kD;
c) it should have either:

1. an affinity for tumor-associated antigens (specific tumor accumulation) or
2. a high turnover rate in tumor tissues (non-specific tumor uptake).

The protein with a maximally long biological half-life remains sufficiently long in the circulation for there to be a considerable increase in the probability of accumulation in the tumor (specific or non-specific).

A molecular weight above 50 kD is advantageous because:
1. The residence time in the tumor tissue as considerably lower for small molecules, because of the high back-diffusion coefficients, than for macromolecules.
2. Proteins with molecular weights below 50 kD are not retained by the kidney but are excreted.

Proteins with high affinity for tumor-associated antigens is are known, for example mono- or polyclonal antibodies or antibody fragments.

Examples of proteins which accumulate by non-specific processes in tumors include serum albumin, fibrinogen, immunoglobulins (IgG, IgM) and lipoproteins.

The conjugates according to the invention can be composed, for example, of one or more polyalcohols which are chemically bonded to a radioactively labeled agent (active agent) and coupled via a linker to an autologous protein which can be taken up specifically or non-specifically. One example of this is the conjugate of the diagrammatic formula III:

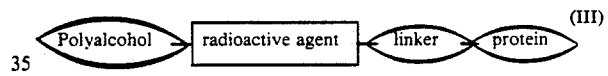

The conjugate is suitable, by reason of its integrated radioactive label, for tumor scintigraphy. Other conjugates according to the invention contain two different active agents or a bifunctional agent, such as the conjugate of the diagrammatic formula IV:

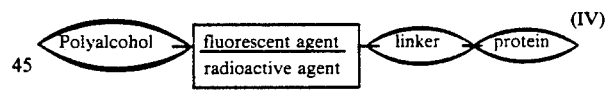

The conjugate of the formula IV has the advantage that it is possible in the first place to determine the time of maximum accumulation in the tumor tissue by means of scintigraphic methods utilizing the radioactive label. It is subsequently possible, utilizing the fluorescence properties of the same agent or of a second agent, to determine accurately the distribution in the tissue or in tissue sections (for example from biopsy samples) by means of fluorescence microscopy.

The radioactive label can be dispensed with if conjugates of the formula IVa are used:

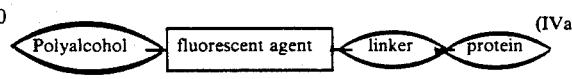

Examples specifically suitable for this use are derivatives of porphyrins, phthalocyanins and naphthalocyanins which are of importance for photodynamic therapy (PDT) with lasers.

Conjugates of the diagrammatic formula V:

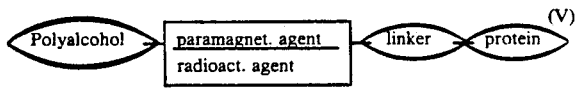

are conjugates according to the invention, in which the active agent contains atoms with a half-integral spin number ($^{13}C$, $^{15}N$, $^{19}F$, $^{31}p$ etc.), in which case the agent acts as nuclear spin label. The polyalcohol can itself be the active agent. Both types of nuclear spin labels can be prepared, for example, by introducing $^{19}F$-containing groups. It is thus possible, by means of nuclear spin tomography, to locate the conjugates of the formula V in the body non-invasively.

Replacement of the signal-emitting active agent by a therapeutically active agent results, for example, in conjugates according to the invention of the diagrammatic formula VI, which are suitable for tumor therapy:

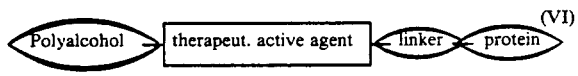

Examples of therapeutic active agents which can be incorporated are photodynamically active substances such as porphyrins, phthalocyanins and naphthalocyanins and derivatives thereof. After incorporation in the tumor tissue, these compounds can be activated from outside by laser light, which results principally in singlet oxygen. This irreversibly oxidizes in a targeted manner cellular macromolecules in the tumor tissue. It is just as good to incorporate substances with cytostatic activity (platinum-containing compounds, iododeoxycytidine, cytosine arabinoside (Ara C), anthracycline derivatives etc.) which display their action in a targeted manner after accumulation in the tumor tissue. It is possible in this way for substances with cytostatic activity to be transported in higher concentrations into the tumor tissue, and to accumulate there, without exposing the patient's normal tissue.

In order to be able to connect together the individual compounds, the polyalcohol, active agent, linker and protein, to give the polyalcohol-active agent-linker-protein conjugates according to the invention, it is preferable for at least the active agent(s) and the linker(s) each to have two functional groups by means of which the chemical bonds between the individual molecules can be produced. Examples of such functional groups are amino or hydroxyl groups, easily replaceable halogen atoms such as are present, for example, in cyanuric chloride, acid halides, carboxylic acids, carboxylic esters such as N-succinimidyl esters, carboxylic anhydrides, diazonium groups or isothiocyanates. Both the polyalcohols and the proteins intrinsically have at least one reactive functional group such as a hydroxyl, carboxyl or amino group. In the case of the active agents and the linkers it may be necessary where appropriate to incorporate one or even two such functional groups into the relevant molecule. This is expediently carried out by processes known from the literature.

The conjugates according to the invention are prepared by chemical linkage, disclosed in the literature, of the individual components, the polyalcohol, active agent, linker and protein. The individual components are preferably linked together covalently. In this connection, it is generally advantageous to apply the following synthesis outline:

1. Coupling of the polyalcohol to the active mono- or bifunctional agent.
2. Where necessary, radioactive labeling, preferably with radioiodine.
3. Reaction of the product of reaction 2., which is radioactively labeled where appropriate, with the linker.
4. Reaction of the conjugate from 3. with the relevant protein to give the desired final product. Where necessary, the conjugate according to the invention which has been obtained in this way is then purified (for example by HPLC) and sterilized.

It has proven expedient first to react the active agent, or the active agents which have already been coupled together, preferably with the addition of 0.8 to 3, preferably 1 to 1.6, mole (based on active agent) of sodium cyanoborohydride ($NaBH_3CN$) with equimolar amounts or with an up to 2-fold, preferably up to 1.3-fold, excess (based on active agent) of the polyalcohol at temperatures from 80° to 120° C., preferably 90° to 110° C., for 10 min to 10 hours, preferably 20 min to 8 hours. The reaction is preferably carried out in the presence of a polar solvent such as ethylene glycol, glycerol or polyethylene glycol with at least two ethylene units and, where appropriate, in the presence of a proton donor such as an organic or inorganic acid such as acetic acid or hydrochloric acid. The temperatures for this reaction are room temperature up to the boiling point, preferably at 80° to 120° C., particularly preferably at 90° to 110° C., and the reaction times are 30 min to 4 weeks, preferably 10 min to 10 hours.

If two or more polyalcohol molecules are to be coupled onto the active agent, it is expedient to incorporate two or more functional groups which can react with the polyalcohol into the active agent. It is advisable in this case to suit the molar amount of polyalcohol which is used to the functional groups present in the active agent. It is also expedient in this case to increase the amount of $NaBH_3CN$ added; preferably to the equimolar to 1.5 times the amount of the functional groups present in the active agent. The reaction temperatures and reaction times correspond to those of the reaction described above. In the case of this reaction too, reaction in the presence of a solvent and, where appropriate, of a proton donor is preferred as for the reaction described above. The reaction temperatures and reaction times likewise correspond to those of the reaction described above.

If radioactively labeled compounds are used as active agents, it is possible, where the radioactively labeled compounds cannot be bought as starting substances, to carry out the labeling with the radioisotope before, but especially after, the reaction with the polyalcohol(s). It is also possible in some cases to carry out the radioactive labeling only after the coupling on of the linker and even after the coupling on of the protein. However, it has proven expedient, for example when radioiodine-labeled tyramine is used as active agent, to carry out the radioiodine labeling on the polyalcoholtyramine conjugate. The radioiodine labeling can be carried out by methods known from the literature. The radioiodine labeling is preferably carried out with a hypochlorite solution of exactly defined pH and $Cl^+$ content. A chlorine solution which is saturated at room temperature has proven expedient (pH=7.4, $[Cl^+]=0.1$ $\mu g/ml$). For the labeling, sufficient of the hypochlorite solution described above is now added to a mixture of the product which is to be labeled and aqueous alkaline radioiodide solution (with a specific activity of 0.1 μg of $^{131}I^-$/MCi of $^{131}$) as is necessary for oxidation of the amount of $^{131}I^-$ employed. A concentration of 0. 2 to 2 μg of Cl+/μg of $^{131}I^-$ has proven expedient for this. The reaction temperature is room temperature and the reaction time is 2 to 30 min. The yields are 90 to 99%. The product can subsequently be treated further without further purification.

If the polyalcohol is to assume the dual function of polyalcohol+active agent, it is advisable to carry out the appropriate derivatization of the polyalcohol before the coupling onto the linker. For this purpose, the polyalcohol is converted into the $C^{19},F_3$, $^{19}F$-akyl, $^{19}F$-phenyl or $^{19}F$ derivatives, for example, by processes known from the literature.

The resulting polyalcohol-active agent conjugate can now be reacted with a linker in a further reaction step. This reaction is likewise carried out by processes known from the literature. The polyalcohol-active agent conjugate is preferably reacted with cyanuric chloride (2,4,6-trichloro-s-triazine). For this, the polyalcohol-active agent conjugate is reacted with 0.8 to 2, preferably 1 to 1.3, mole-equivalents (based on the polyalcohol-active agent conjugate) of cyanuric chloride at temperatures from 4° to 30° C., preferably 18° to 22° C. The reaction time is 1 to 5 minutes, preferably 2 to 3 minutes. The reaction is particularly preferably carried out in a solvent such as phosphate buffer (pH 7.4), dimethylacetamide or mixtures thereof. The reaction temperatures and reaction times in this case are also those indicated above. If cyanuric chloride is linked via the terminal hydroxyl group of the radioiodine-labeled tyramine, this has the additional advantage that the radioactive iodine located in the ortho position to the OH group of tyramine is, after the formation of an ether bridge to the triazine molecule, linked more securely to the benzene ring of tyramine, which avoids the all too easy deiodination which is often observed with radioiodine diagnostic agents of the state of the art in the organism.

The polyalcohol-active agent-linker conjugate obtained in this way is reacted with the protein in the final reaction step. This reaction can also be carried out by processes known from the literature. With the preferred use of cyanuric chloride as linker, the protein is coupled on via the functional group which is still free (a chlorine atom) on the cyanuric chloride with the formation of an ether, thio or amino bridge, depending on which amino acid of the protein supplies the linkage.

To carry out this reaction, the polyalcohol-active agentlinker conjugate is reacted with equimolar to twice the molar amounts, preferably equimolar amounts, of the appropriate protein. The temperatures for this reaction are 4° to 30° C., preferably 18° to 22° C. The reaction times are 10 to 60 minutes, preferably 30 to 40 minutes. This reaction is also preferably carried out in a solvent such as phosphate buffer (pH 7.4 to 8.5) with or without addition of dimethylacetamide. The reaction temperatures and times indicated above also apply in this case.

The conjugates according to the invention can also be prepared by any desired interchange of the process steps described above, as long as it is ensured that the resultant sequence of molecules is polyalcohol-active agent-linker-protein.

The conjugates according to the invention are isolated and purified, where appropriate after concentration by centrifugation in ®AMICON C30-C100 cells, for example by HPLC. The sterilization which is necessary where appropriate is carried out, for example, through 0.22 μm sterile filters.

The starting substances needed for the preparation of the conjugates according to the invention can, where they cannot be bought, be prepared in a straightforward manner by processes known from the literature.

The conjugates according to the invention can, after purification and sterilization, be either administered immediately or previously mixed with a suitable solvent. Examples of suitable solvents are physiological saline or phosphate buffer (pH 7.4; 287 mosm), as well as sugar solutions such as glucose or mannitol solutions, or else mixtures of the various solvents mentioned. Injectable compositions which have proven expedient for diagnostic use are those which contain the conjugates according to the invention in concentrations of 1 to 10 mg/ml, preferably about 4 mg/ml. Conjugate concentrations of 40 to 50 mg/ml are advisable for therapeutic use.

In the case of conjugates which contain a radioactive label or a radiopharmaceutical, it is advisable to prepare these only shortly before use, because this makes it easier to adjust the radiation dose required for therapy or necessary for diagnosis. In particular, synthesis shortly before use is appropriate if the conjugates according to the invention contain radionuclides with short half-lives.

The injectable compositions according to the invention can be injected into patients suspected of having tumors in amounts of 1 to 20 ml, preferably 2 to 5 ml. 24 to 72 hours, preferably 48 to 72 hours, after the injection it is then possible to locate the tumor(s) by means of an external scanning device which is tuned to the active agent used, or in the case where the active agent has to be initiated by an external device (for example in therapeutic treatment with photoactive substances), it is possible to carry out the initiation after this time at the latest.

EXAMPLES

EXAMPLE 1

Preparation of tyramine-N-1'-deoxysorbitol (TDS)

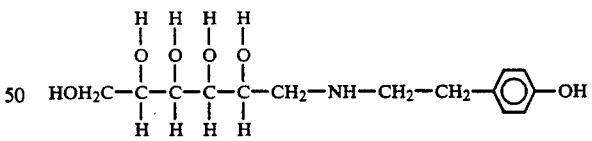

34.8 mg of tyramine ×HCl (0.2 mmol) (manufacturer: Serva, Heidelberg) are dissolved together with 50 mg of D(+)-glucose monohydrate (about 0.25 mmol) (manufacturer: E. Merck, Darmstadt) in 1 ml of ethylene glycol, heating cautiously. Then 20 mg of sodium cyanoborohydride (about 0.3 mmol) (manufacturer: E. Merck, Darmstadt) are added and the reaction mixture is heated in a glycerol bath at 100° C. for 30 min. The solution is cooled and then diluted with 9 ml of distilled H2O. The solution prepared in this way can be used immediately for analysis or separation of the components by HPLC.

HPLC conditions:

Precolumn: C18 20 μm, 50 × 4 mm (from Latek,

| | |
|---|---|
| Column: | Heidelberg)<br>Nucleosil 10 SA, 250 × 4 mm (from Latek, Heidelberg) |
| Eluent: | 0.1 M NH₄ acetate, pH 6.0, 90%<br>acetonitrile 10% |
| Flow rate: | 1 ml/min |
| UV detector: | 280 nm |
| Retention times: | 1) unknown component: 6.55 min<br>2) tyramine-N-1'-deoxysorbitol: 7.80 min<br>3) tyramine: 8.90 min |

The yield according to the HPLC is about 75–80%.

EXAMPLE 2

Radioactive labeling of tyramine-N-1'-deoxysorbitol (TDS) with radioiodine ($^{131}$I)

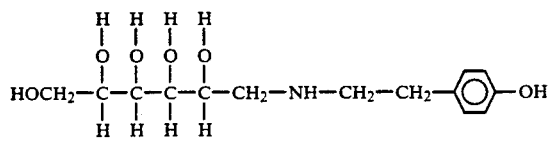

25 μg of TDS (0.08 pmol) dissolved in 25 μl of 0.13M phosphate buffer (pH 7.4) are mixed at room temperature with an aqueous alkaline solution (pH 8–11) of radioiodine (up to 10 mCi of $^{131}$I, corresponding to an amount of about 1 μg of iodine). 5 to 10 μl of a sodium hypochlorite solution (0.1 μg of Cl⁺/μl of phosphate buffer pH 7.4) are added per mCi of radioiodine ($^{131}$I) to convert the radioiodide into the reactive iodonium ion (I⁺) which in turn replaces, by electrophilic substitution, a proton ortho to the hydroxyl group on the phenyl ring.

Labeling yield: 95 to 98%

Thin-layer chromatography:

| | | | | |
|---|---|---|---|---|
| Mobile phase: | acetone,<br>60 | 1-butanol,<br>25 | 25% ammonia,<br>10 | dist. H₂O<br>5 (v/v) |
| Plates: | Silica gel 60 (5 × 20 cm) without fluorescence indicator (E. Merck, Darmstadt, FRG) | | | |
| Development distance: | 10 cm | | | |
| Rf.: | $^{131}$I-TDS | 0.4 to 0.45 | | |
| | $^{131}$I-iodide | 0.94 | | |

EXAMPLE 3

Reaction of $^{131}$I-TDS from Example 2 with cyanuric chloride:

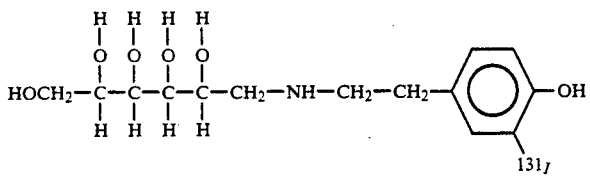

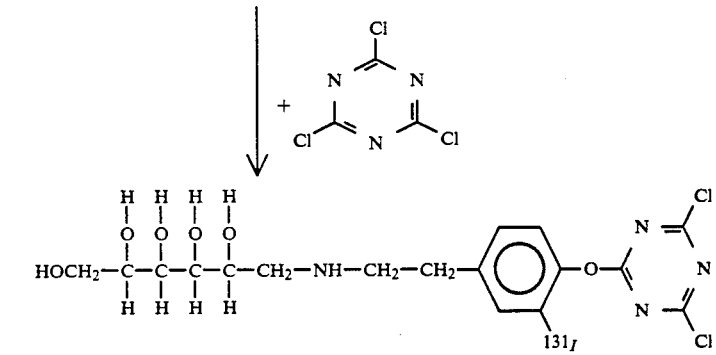

For the reaction of $^{131}$I-TDS with cyanuric chloride, first a solution of cyanuric chloride in anhydrous 1,4-dioxane (10 mg/ml) is prepared.

1.3 times the theoretically required amount of cyanuric chloride (20 μg of cyanuric chloride, corresponding to 2 μl of the dioxane solution prepared above) is added to the solution of $^{131}$I-TDS (based on 25 μg of TDS). The reaction is complete 2 to 3 minutes after the cyanuric chloride addition at room temperature.

EXAMPLE 4.1

Reaction of $^{131}I$-TDS-dichlorotriazine from Example 3 with rat serum albumin

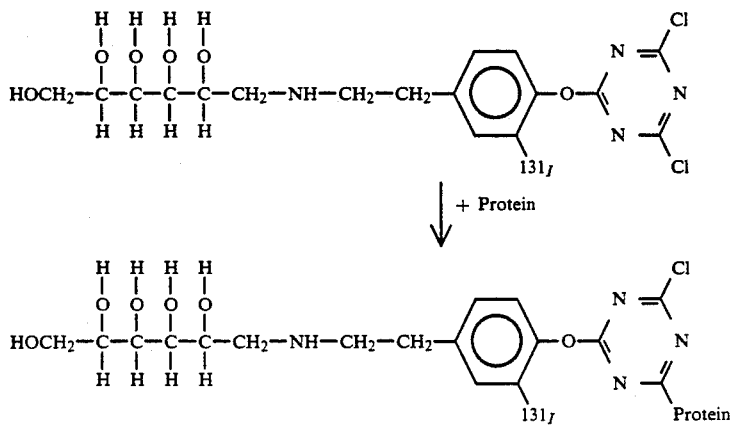

To couple the compound $^{131}I$-TDS-dichlorotriazine resulting from Example 3 with rat serum albumin (about 70 kD), the equimolar amount of the protein, dissolved in phosphate buffer (25 mg/ml, pH 8.3), is added. The amount of rat serum albumin based on 25 μg of TDS is 5.8 mg. The coupling yield after a reaction time of 30 to 40 minutes at room temperature is 80 to 85%.

EXAMPLE 4.2

In analogy to Example 4.1, $^{131}I$-TDS-dichlorotriazine (from Example 3) is reacted with rat IgG (about 150 kD). The required amount of rat IgG is 12.5 mg. The coupling yield is 80 to 85%.

EXAMPLE 4.3

In analogy to Example 4.1, $^{131}I$-TDS-dichlorotriazine (from Example 3) is reacted with fibrinogen (about 350 kD). The required amount of fibrinogen is 30 mg. The coupling yield is 80 to 85%.

EXAMPLE 5

Preparation of 4-amino-1,8-naphthalic acid tyrimide (ANT)

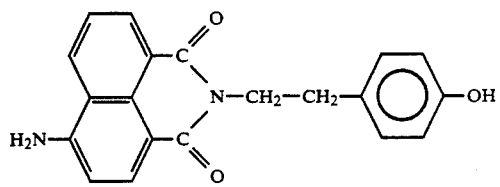

426 rAg of 4-amino-1,8-naphthalic anhydride (2 mmol) (manufacturer: Aldrich-Chemie, Heidenheim) are dissolved together with 1.37 g of tyramine (10 mmol) (manufacturer: Aldrich-Chemie, Heidenheim) in 30 ml of dimethylformamide (DMF) and heated in a glyercol bath at 140° C. for 30 min. The DMF is stripped off in a rotary evaporator under oilpump vacuum, and the residue is boiled under reflux with 100 ml of 6N HCl for 2.5 h. After the solution in hydrochloric acid has cooled, the brownish yellow sediment is filtered off, dissolved in a hot mixture of 50 ml of methanol and 50 ml of ethanol and reprecipitated by addition of 300 ml of 6N HCl. The precipitation is completed by storing the solution at +4° C. for 2 hours. The sediment is filtered off and dried in a desiccator. Yield: 498 mg (about 75% of theory).

Analysis:

1. Thin-layer chromatography:

| | | | | |
|---|---|---|---|---|
| Mobile phase: | acetone, 60 | 1-butanol, 25 | 25% ammonia, 10 | dist. H₂O 5 (v/v) |
| Plates: | silica gel 60 (5 × 20 cm) without fluorescence indicator (E. Merck, Darmstadt, FRG) | | | |
| Development distance: | 10 cm | | | |
| Rf.: | 4-Amino-1,8-naphthalic acid tyrimide: 0.88–0.92 (the substance displays an intense yellowish green fluorescence and has an absorption maximum at 445 nm). | | | |

2. HPLC:

| Conditions | |
|---|---|
| Sample volume: | 100 μl |
| Precolumn: | 50 × 4 mm; C18 30μ |
| Column: | 250 × 10 mm; C18 5μ GO |
| Eluent: | A: 0.1% formic acid in water 40% B: methanol 60% |
| Gradient: | 60–100% methanol in 12 min; Exponent 2 |
| Delay time: | 2 min |
| Flow rate: | 4 ml/min |
| $\lambda_{uv}$: | 445 nm |
| Retention time: | 11.4 min |

EXAMPLE 6

Preparation of 4-amino-1, 8-naphthalic acid tyrimide-N-1'-deoxysorbitol (ANT-N-1'-deoxysorbitol)

EXAMPLE 7

Radioactive labeling of ANT-N-1'-DS with radioiodine

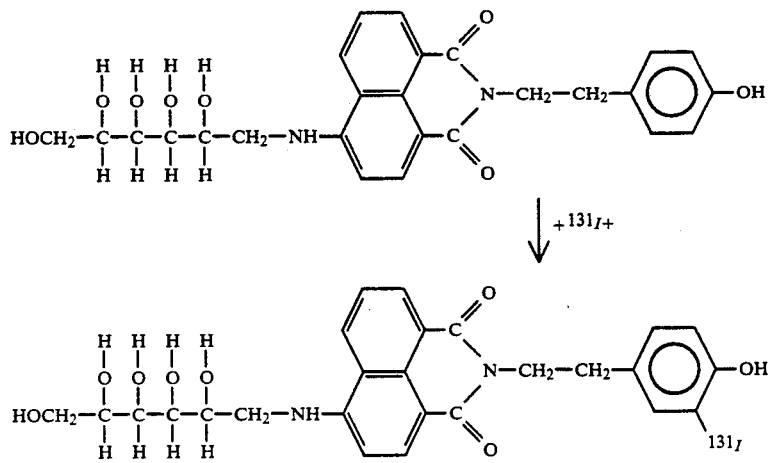

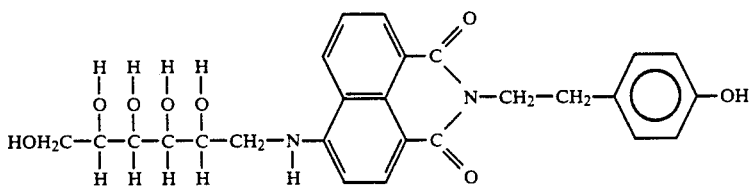

10 mg of ANT (30 μmol) from Example 5 are dissolved together with 200 mg of glucose monohydrate (about 1 mmol) (manufacturer: E. Merck, Darmstadt) and 68 mg of sodium cyanoborohydride (about 1.1 mmol) (manufacturer: E. Merck, Darmstadt) in 1 ml of ethylene glycol and 0.3 ml of 25% acetic acid and heated in a glycerol bath at 100° C. for 5 h. After the reaction solution had cooled, ANT and ANT-N-1'-deoxysorbitol were removed from the reaction mixture by HPLC prepurification.

Column: Nucleosil C18 20 μm, 100×10 Mm
Eluent: 0.1% formic acid in water
Flow rate: 3 ml/min
Loaded vol.: 500 μl After 5 min the solvent was changed and ANT and ANT-N-1'-deoxysorbitol were eluted from the column with 100% methanol.

ANT and ANT-N-1'-deoxysorbitol were separated under the same HPLC conditions used for ANT identification.

Retention time:
ANT-N-1'-deoxysorbitol: 8.55 min
ANT: 11.40 min

The yield resulting after removal of the mobile phase was 3 mg (about 20% of theory).

50 μg of ANT-N-1'-DS (about 0.1 /μmol) from Example 6, dissolved in 100 μl of a mixture of 0.13M phosphate buffer (pH 7.4) and dimethylacetamide (70:30), are mixed with an aqueous alkaline (pH 8 to 11) solution of radioiodine (up to 10 MCi of $^{131}I$ corresponding to an amount of about 1 μg of iodine). 5 to 10 μl of a sodium hypochlorite solution (0.1 μg of $Cl^+$/μl of phosphate buffer pH 7.4) are added per mCi of radioiodine ($^{131}I$) to convert the radioiodide into the reactive iodonium ion ($I^+$) which in turn replaces, by electrophilic substitution, a proton ortho to the hydroxyl group on the phenyl ring.

Labeling yield: 95 to 98%
Analysis: Thin-layer chromatography

| Mobile phase: | acetone, | 1-butanol, | 25% ammonia, | dist. $H_2O$ |
|---|---|---|---|---|
| | 60 | 25 | 10 | 5 (v/v) |
| Plates: | silica gel 60 (5 × 20 cm) without fluorescence indicator (E. Merck, Darmstadt, FRG) | | | |
| Development distance: | 10 cm | | | |
| Rf.: | $^{131}I$-ANT-N-1'-DS: | | 0.44–0.48 | |
| | $^{131}I$-iodide | | 0.94 | |

EXAMPLE 8

Reaction of ¹³¹I-ANT-N-1'-DS with cyanuric chloride:

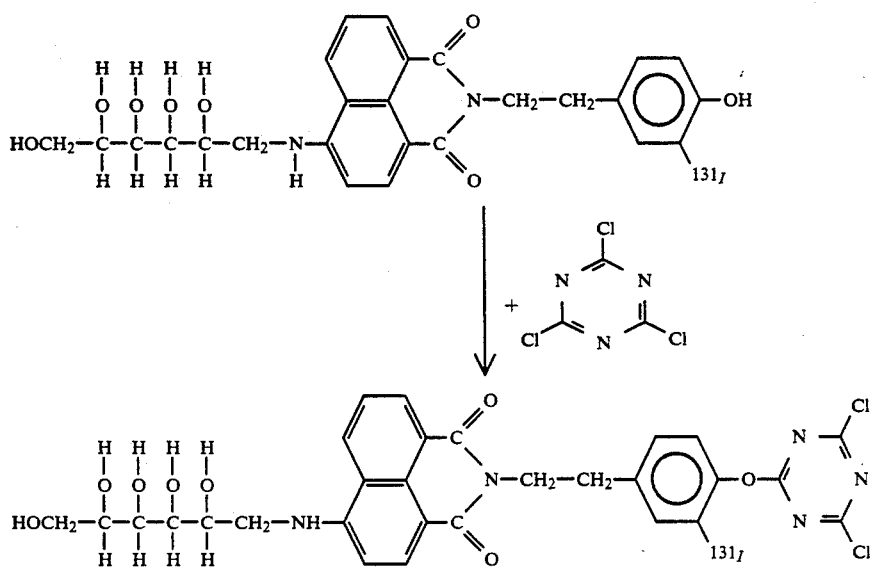

For the reaction of ¹³¹I-ANT-N-1'-DS from Example 7 with cyanuric chloride, firstly a solution of cyanuric chloride in anhydrous 1,4-dioxane (10 mg/ml) is prepared. For an equimolar reaction, 1.3 times the theoretically required amount of cyanuric chloride (24.5 µg cyanuric chloride corresponding to 2.5 µl of the previously prepared dioxane solution) is added to the solution of ¹³¹I-ANT-N-1'-DS (based on 50 µg of ANT-N-1'-DS). The reaction is complete 2 to 3 min after the addition of cyanuric chloride at room temperature.

EXAMPLE 9.1

Reaction of ¹³¹I-ANT-N-1'-DS-dichlorotriazine with rat serum albumin protein-labeling yield after a reaction time of 30 to 40 minutes at room temperature is about 80%.

The labeled protein is purified by HPLC:
Pump: P 400 (from Latek, Heidelberg, FRG)
Eluent: 0.2M sodium phosphate pH 7.4
Flow rate: 1 ml/min
Precolumn: 50×4 mm, Zorbax Diol
Column I: Zorbax GF 450 (from DuPont, Dreieich, FRG)
Column II: Zorbax GF 250
UV detector: Single path monitor UV-1 (from Pharmacia, Freiburg, FRG)
γdetector: NaI 1.5"×21"with Berthold Electronics
Recorder: Shimadzu, Chromatopac C-RLA (from Latek)
Retention time: 19.8 min

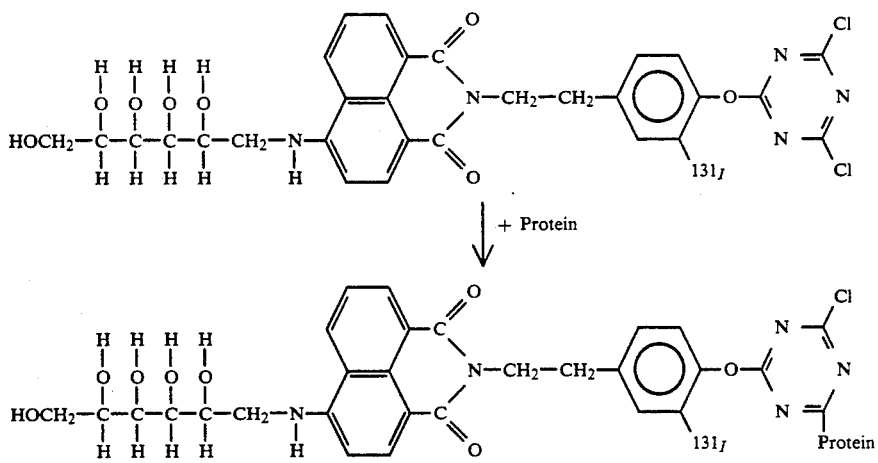

To couple the compound resulting from Example 8, ¹³¹I-ANT-N-1'-DS-dichlorotriazine, with rat serum albumin (about 70 kD), the equimolar amount of the protein, dissolved in phosphate buffer (25 mg/ml, pH 8.3), is added. The amount of rat serum albumin based on 50 µg of ANT-N-1'-DS is 7 mg. The coupling and

EXAMPLE 9.2

In analogy to Example 9.1, $^{131}$I-ANT-N-1'-DS-dichlorotriazine (from Example 8) is reacted with rat IgG (about 150 kD). The required amount of rat IgG is 15 mg. The protein-labeling yield is 80%. Purification is by HPLC as described in Example 9.1. Retention time: 18.2 min

EXAMPLE 9.3

In analogy to Example 9.1, $^{131}$I-ANT-N-1'-DS-dichlorotriazine (from Example 8) is reacted with fibrinogen (about 350 kD). The required amount of fibrinogen is 35-37 mg. The protein-labeling yield is 80%. Purification is by HPLC as described in Example 9.1.

Retention time: 15.0 min

PHARMACOLOGICAL EXAMPLES

Figure 2:
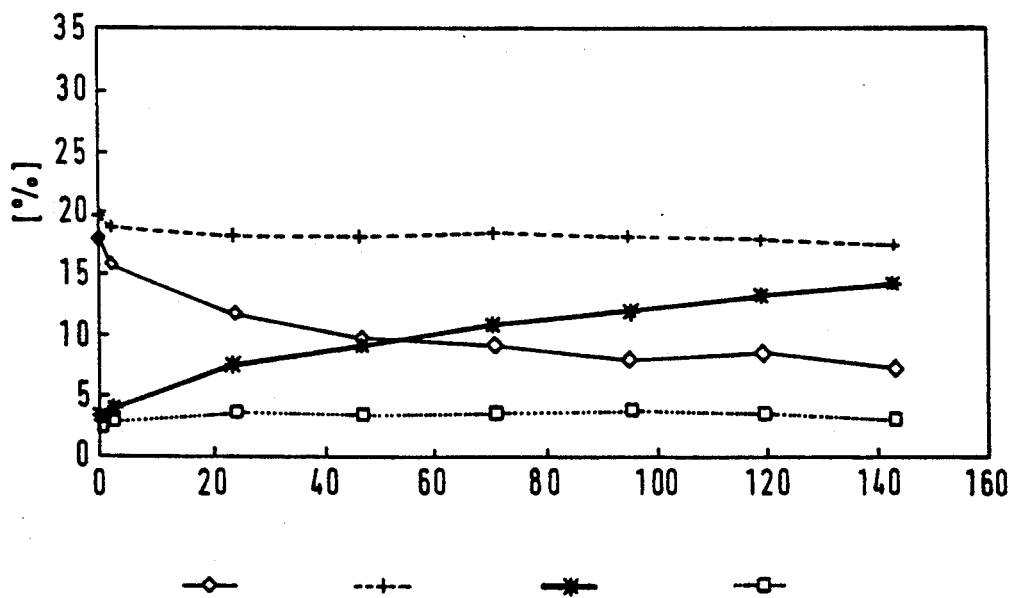
FIG. 2. The percentage radioactivity distribution (based on administered radioactivity) in the heart (— ◊ —), liver (—+—), tumor (—*—) and muscle (—□—) of $^{131}$I-TDS-IgG (tryamine-deoxysorbitol coupled to rat IgG) measured as a function of time in BD IX rats with implanted ovarian carcinoma. For experimental details, see "Pharmacological Examples."

To demonstrate the high tumor-accumulation rate of the conjugates according to the invention, the latter are injected into experimental animals which have previously received a tumor implant. The percentage activity distribution (based on administered activity) in the heart, liver, tumor and muscle of various conjugates according to the invention which contained a radioactive label as active agents was measured as a function of time. The changes in activity are shown in FIGS. 1 and 2.

Animal experiment with $^{131}$I-TDS-RSA (tyranLine-deoxysorbitol coupled to rat serum albumin, substance from Example 4.1)

Recording apparatus: γcamera (Searle, Pho-Gamma IV, FLOV)
Data acquisition apparatus: Gaede, medworker N 4
Data acquisition mode: Frame mode
Matrix: 128×128
Animal model: rat, BD IX, female
Age: 8 weeks
Weight: 200-220 g
Number of animals: 4
Tumor: ovarian carcinoma (0-342, Zeller, DKFZ)
Type of implant: intramuscular
Number of cells implanted: $5 \times 10^6$
Site of implantation: left rear limb
Start of experiment: 10 days after tumor transplantation
Tumor diameter at start of experiment: 15-18 EM
Duration of experiment: 72 hours
Mode of administration of $^{131}$I-TDS-RSA: intravenous
Site of administration: lateral tail vein
Amount of activity administered: 300 μCi (11.1 mBq) $^{131}$I
is Volume administered: 0.3 ml
Solvent: phosphate buffer (PPB), 0.13M, pH 7.4
Spec. activity: 1 mCi (37 MBq)/5 μg of TDS ×1 mg of RSA ×1 ml of PPB
Amount of protein administered: 0.3 mg (corresponding to 0.3 mCi)
Recording times: 10 min and 1, 2, 4, 18, 48 and 72 h after injection
Duration of recording: 5 min
Tumor diameter at the end of the experiment: 20-22 mm
The activity distribution is depicted in FIG. 1.

Animal experiment with $^{131}$I-TDS-IgG (tyrainine-deoxysorbitol coupled to rat IgG, substance from Example 4.2)

Recording apparatus: γ camera (Searle, Pho-G.Rmm-9 IV, FLOV)
Data acquisition apparatus: Gaede, medworker N 4
Data acquisition mode: Frame mode
Matrix: 128×128
Animal model: rat, BD IX, female
Age: 8 weeks
Weight: 200-220 g
Number of animals: 4
Tumor: ovarian carcinoma (0-342, Zeller, DKFZ)
Type of implant: intramuscular
Number of cells implanted: $5 \times 10^6$
Site of implantation: left rear limb
Start of experiment: 10 days after tumor transplantation
Tumor diameter at start of experiment: 10-12 mm
Duration of experiment: 144 hours
Mode of administration of $^{131}$I-TDS-IgG: intravenous
Site of administration: lateral tail vein
Amount of activity administered: 125 μCi (11.1 MBq) $^{131}$I
Volume administered: 0.3 ml
Solvent: phosphate buffer (PPB), 0.13M, pH 7.4
Spec. activity: 1 mCi (37 MBq)/2.5 μg of TDS ×1 mg of IgG ×1 ml of PPB
Amount of protein administered: 0.125 mg (corresponding to 0.125 mCi)
Recording times: 10 min and 1, 2, 4, 18, 48, 72, 96, 120 and 144 h
Duration of recording: 5 min
Tumor diameter at the end of the experiment: about 20 mm
The activity distribution is depicted in FIG. 2.

We claim:

1. A conjugate comprising:
   (a) at least one polyalcohol or a derivatized polyalcohol, wherein said polyalcohol(s) or derivatized polyalcohol(s) are not recognized by the defense system of an organism as exogenous and are sorbitol or derivatized sorbitol, with at least one OH group being replaced by $^{19}$F, $C^{19}F_3$, mono- or poly-$^{19}$F-substituted $C_1$-$C_4$alkyl, mono-, di-, tri-, tetra or penta-$^{19}$F-substituted phenyl,
   (b) at least one active agent,
   (c) at least one linker, wherein said linker(s) are cyanuric chloride, and
   (d) a protein, wherein said protein is autologous serum albumin, said components being connected together covalently in the order (a)-(b)-(c)-(d).

2. A conjugate as claimed in claim 1, wherein said derivatized polyalcohol(s) which is or are not recognized as exogenous by the defense system of an organism assumes the function of said active agent, or wherein said linker assumes the function of said active agent(s).

3. A conjugate as claimed in claim 1, wherein the active agent(s) are selected from the compounds of the Formula II

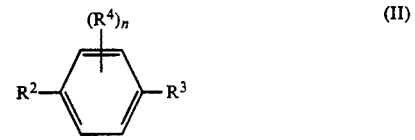

in which in which
$R^2$ is $NH_2$, $C_1$-$C_4$-alkylamino or CHO,
$R^3$ is $NO_2$, $NH_2$, OH or NCS,
$R^4$ is $^{131}$I, $^{123}$I, $^{19}$F, $C^{19}F_3$, OH or H, and n is 1 to 4.

4. A conjugate according to claim 1, wherein component (a) is composed of only one sorbitol or derivatized sorbitol.

5. A conjugate according to claim 1, wherein component (b) is composed of one or two active agents.

6. A conjugate according to claim 1, wherein component (c) is composed of one linker.

7. A conjugate according to claim 1, wherein the active agent(s) of component (b) are selected from the group consisting of a radioactively labeled compound, a fluorescence label, an NMR label, an ESR label, a photoactive compound and a cytostatic agent.

8. An agent for the therapy of tumors, containing at least one conjugate as claimed in claim 1, wherein the active agent(s) of component (b) is a therapeutically active agent.

9. An agent for diagnosing tumors, containing at least one conjugate as claimed in claim 1, wherein the active agent(s) of component (b) is a diagnostic agent.

* * * * *